April 30, 1968 R. KORDES Plant Pat. 2,810
ROSE PLANT
Filed Jan. 19, 1967
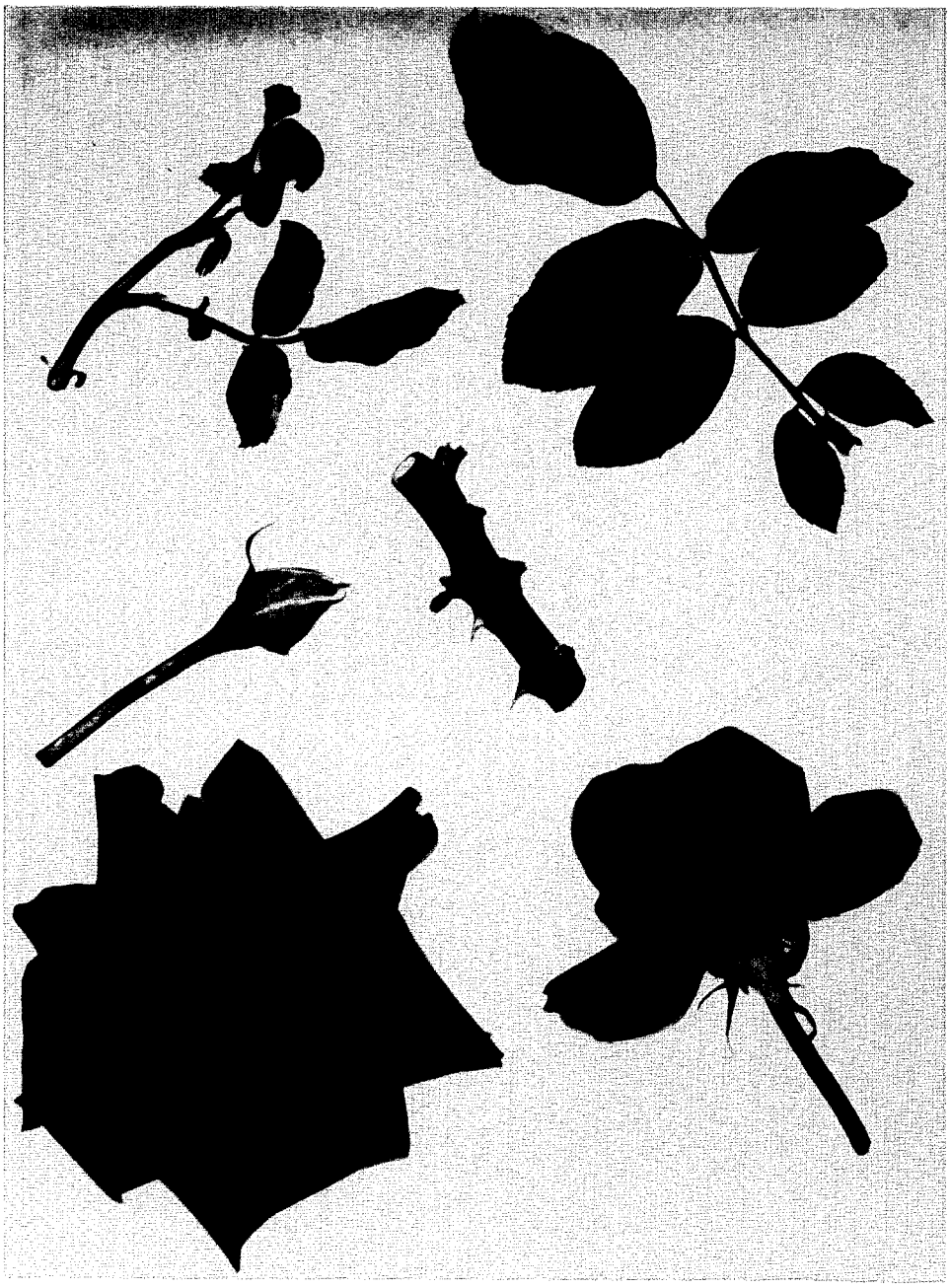
Inventor.
Reimer Kordes
By: Robb & Robb
Attorneys.

United States Patent Office

Plant Pat. 2,810
Patented Apr. 30, 1968

2,810
ROSE PLANT

Reimer Kordes, Barmstedt, near Elmshorn, Germany, assignor to Jackson & Perkins Company, Newark, N.Y., a corporation of New York Filed Jan. 19, 1967, Ser. No. 610,458
1 Claim. (Cl. Plt.—20)

The present invention relates to a new and distinct variety of rose plant of the hybrid tea class, which was was originated by me by crossing an unnamed and unpatented seedling of "Spartan" (U.S. Plant Patent No. 1,357)×"Prima Ballerina" (unpatented) with the variety known as "Karl Herbst" (unpatented).

The primary objective of this breeding was to produce a new rose variety which bears flowers larger in size than those of "Spartan" while retaining a flower color similar to that of "Karl Herbst." This objective was fully achieved, along with other desirable features, as evidenced by the following unique combination of characteristics which are outstanding in the new variety and which distinguish it from its parents, as well as from all other varieties of which I am aware:

(1) A very vigorous plant habit;
(2) A flower size larger than that of "Spartan";
(3) A quilled form of the outer petals of the flower; and
(4) A distinctive and attractive Spectrum Red flower color.

Asexual reproduction of the new variety by budding, as performed at Newark, N.Y., U.S.A. and also at Pleasanton, Calif., U.S.A., shows that the foregoing characteristics and distinction come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—An unnamed seedling of "Spartan" ×"Prima Ballerina."
*Pollen parent.*—"Karl Herbst."
Classification:
*Botanic.*—Hybrid tea.
*Commercial.*—Hybrid tea.

*Flower*

(Observations made from specimens grown outdoors at Newark, N.Y., U.S.A., in the early morning during the latter part of the month of September.)

Blooming habit: Recurrent—continuous.
Bud:
*Size.*—Medium.
*Form.*—Short and pointed; is not affected by wet or hot weather.
*Color.*—When sepals first divide—Bordeaux, Plate 12. When petals begin to unfurl—Pomegranate Purple, Plate 12, very lightly overcast with Bordeaux, Plate 12. When half-blown: inside of petals—Nopal Red, Plate 1, very lightly overcast with Scarlet-Red, Plate 1; reverse of petals—Carmine, Plate 1, very lightly overcast with Nopal Red, Plate 1.
*Sepals.*—Slightly branched; curl back when petals begin to unfurl.
*Calyx.* — Shape — funnel. Size — small. Aspect — smooth. Odor when rubbed—none.
*Peduncle.* — Length — medium. Aspect — smooth. Strength—erect; heavy. Color—Brick Red, Plate 13.
*Opening.*—Opens up well; is not affected by adverse weather conditions.

Bloom:
*Size.*—medium. Average size when fully expanded—4½ inches.
*Borne.*—Both singly and several together.
*Stems.*—From medium length to long; strong.
*Form.* (when first open).—High-centered. Permanence—flattens and outer petals quill.
*Petalage.*—Double (full but open center). Number of petals under normal conditions—40.
*Color.*—Center of flower—Scarlet-Red, Plate 1. Outer petals—Nopal Red, Plate 1, lightly overcast with Scarlet-Red, Plate 1. Base of petals (aiglet)—Lemon-Chrome, Plate 4. Inside of petals—Spectrum Red, Plate 1. Reverse of petals—Nopal Red, Plate 1. General tonality from a distance—Spectrum Red, Plate 1.
*Discoloration.*—General tonality at end of first day—Scarlet-Red, Plate 1. Second day—Spectrum Red, Plate 1, very lightly overcast with Scarlet-Red, Plate 1. Third day—Spectrum Red, Plate 1.

Petals:
*Texture.*—Thick; is not affected by wet or hot weather.
*Apperance.*—Inside—shiny. Outside—satiny.
*Form.*—Round; slightly nocked; the outer petals quill.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, Anthers: Medium size; many; regularly arranged around styles. Color—Antimony Yellow, Plate 15.
Stamens filaments (threads): Medium length. Color—Naphthalene Yellow, Plate 16.
Pollen: Color—Warm Buff, Plate 15.
Styles: Loosely separated; uneven length; medium length; thin.
Stigmas: Color—Naples Yellow, Plate 16.
Ovaries: All enclosed in calyx.
Hips: none.
Seeds: None.

*Plant*

Form: Bush.
Growth: Very vigorous; upright.
Foliage: Compound of 3–5–7 leaflets.
*Size.*—Medium.
*Quantity.*—Normal.
*Color.*—New foliage: upper side—Mignonette Green, Plate 31, overcast lightly with Madder Brown, Plate 13; under side—Van Dyke Red, Plate 13. Old foliage: upper side—Yew Green, Plate 31; under side—Kronberg's Green, Plate 31.
*Shape.*—Oval pointed.
*Texture.*—Upper side—leathery. Under side—smooth.

*Ribs and veins.*—Ordinary.
*Edge.*—Serrated (saw toothed).
*Serration.*—Both double and single; small.
*Leaf Stem.*—Color—Yellowish-Olive, Plate 30. Under side—prickly.
*Stipules.*—Medium length; slightly bearded.

Wood:

*New wood.*—Color—Acajou Red, Plate 13. Bark—rough.
*Old wood.*—*Color*—Elm Green, Plate 17. Bark—rough.

Thorns:

*Thorns.*—Quantity: on main stalks from base—ordinary; on laterals from stalk—ordinary. Form—narrow base; medium length; hooked downward. Color (when young)—Old Rose, Plate 13. Position—irregular.

*Prickles.*—Quantity: on main stalks—none. on laterals—none.
*Short needles.*—Quantity: on main stalks—none; on laterals—none.

I claim:

1. A new and distinct variety of rose plant of the hybrid tea class, substantially as herein shown and described, characterized particularly as to novelty by the unique combination of a very vigorous plant habit, a flower size larger than that of "Spartan" (U.S. Plant Patent No. 1,357), a quilled form of the outer petals of the flower, and a distinctive and attractive Spectrum Red flower color.

No references cited.

ROBERT E. BAGWILL, *Primary Examiner.*